(12) United States Patent
García Gómez et al.

(10) Patent No.: US 10,596,189 B2
(45) Date of Patent: Mar. 24, 2020

(54) EMULSION AND METHOD FOR THE MANUFACTURE THEREOF

(71) Applicant: BLUE SEA LABORATORIES, S.L., Alicante (ES)

(72) Inventors: Juan Ramón García Gómez, Alicante (ES); Jorge Díaz-Crespo Cardona, Alicante (ES)

(73) Assignee: BLUE SEA LABORATORIES, S.L., Alicante (ES)

( * ) Notice: Subject to any disclaimer, the term of this patent is extended or adjusted under 35 U.S.C. 154(b) by 0 days.

(21) Appl. No.: 16/079,224

(22) PCT Filed: Jan. 29, 2018

(86) PCT No.: PCT/ES2018/070063
§ 371 (c)(1),
(2) Date: Aug. 23, 2018

(87) PCT Pub. No.: WO2018/146354
PCT Pub. Date: Aug. 16, 2018

(65) Prior Publication Data
US 2019/0054114 A1    Feb. 21, 2019

(30) Foreign Application Priority Data
Feb. 7, 2017   (ES) .................................. 201730139

(51) Int. Cl.
| | | |
|---|---|---|
| *A61K 8/06* | (2006.01) | |
| *A61P 17/00* | (2006.01) | |
| *A61K 33/00* | (2006.01) | |
| *A61K 9/00* | (2006.01) | |
| *A61K 9/107* | (2006.01) | |
| *A61K 47/02* | (2006.01) | |
| *A61K 47/08* | (2006.01) | |
| *A61K 47/32* | (2006.01) | |
| *A61K 47/10* | (2017.01) | |
| *A61K 47/22* | (2006.01) | |
| *A61K 8/81* | (2006.01) | |
| *A61K 8/96* | (2006.01) | |
| *A61Q 19/00* | (2006.01) | |
| *A61K 8/34* | (2006.01) | |
| *A61K 8/86* | (2006.01) | |
| *A61K 8/26* | (2006.01) | |
| *A61K 8/37* | (2006.01) | |
| *A61K 47/14* | (2017.01) | |

(52) U.S. Cl.
CPC ................ *A61K 33/00* (2013.01); *A61K 8/06* (2013.01); *A61K 8/26* (2013.01); *A61K 8/34* (2013.01); *A61K 8/342* (2013.01); *A61K 8/345* (2013.01); *A61K 8/37* (2013.01); *A61K 8/8147* (2013.01); *A61K 8/8158* (2013.01); *A61K 8/86* (2013.01); *A61K 8/965* (2013.01); *A61K 9/0014* (2013.01); *A61K 9/107* (2013.01); *A61K 47/02* (2013.01); *A61K 47/08* (2013.01); *A61K 47/10* (2013.01); *A61K 47/22* (2013.01); *A61K 47/32* (2013.01); *A61Q 19/00* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 9,579,266 B2 | 2/2017 | Sasaki et al. | |
| 2009/0258085 A1* | 10/2009 | Bach ........................ | A61K 8/06 424/600 |

FOREIGN PATENT DOCUMENTS

| | | |
|---|---|---|
| ES | 2 593 682 T3 | 12/2016 |
| FR | 2 794 023 A1 | 12/2000 |
| JP | H11-228377 A | 8/1999 |
| WO | 99/02128 A1 | 1/1999 |

OTHER PUBLICATIONS

International Search Report of PCT/ES2018/070063, dated Apr. 16, 2018.

* cited by examiner

*Primary Examiner* — Brian Gulledge
(74) *Attorney, Agent, or Firm* — Collard & Roe, P.C.

(57) ABSTRACT

The invention relates to an emulsion containing a mixture of an aqueous phase and an oil phase, wherein the aqueous phase comprises seawater, a viscosifier, and a humectant, and wherein the oil phase comprises polyglyceryl, hectorite, propylenecarbonate, t-butyl alcohol, a polyacrylate crosspolymer-6, at least one viscosifier, at least one emulsifier, at least one co-emulsifier, and at least one emollient, such that the phases forming the emulsion are stabilized. Another object of the present invention is the method of manufacture, which allows producing the emulsion with seawater described herein in detail.

9 Claims, No Drawings

EMULSION AND METHOD FOR THE MANUFACTURE THEREOF

CROSS REFERENCE TO RELATED APPLICATIONS

This application is the National Stage of PCT/ES2018/070063 filed on Jan. 29, 2018, which claims priority under 35 U.S.C. § 119 of Spanish Application No. P201730139 filed on Feb. 7, 2017, the disclosures of which are incorporated by reference. The international application under PCT article 21(2) was not published in English.

OBJECT OF THE INVENTION

The present invention relates to a stabilized emulsion that has been prepared with seawater for the purpose of enabling the topical application in an easy and rapidly absorbed manner, providing to the skin the emollience properties that are characteristic of the hydrolipidic emulsion and reinforcing the barrier effect with an accelerated natural skin repair process due to the seawater.

In that sense, the emulsion contains a mixture of an aqueous phase and another oil phase, wherein the aqueous phase comprises, among other elements, seawater, a viscosifier, and a humectant, and wherein the oil phase comprises, among other elements, polyglyceryl, hectorite, propylenecarbonate, t-butyl alcohol, polyacrylate crosspolymer-6.

The object of the invention is to achieve a lightweight emulsion that is both physically and microbiologically stable and has beneficial properties resulting from the presence of the seawater.

BACKGROUND OF THE INVENTION

The properties of seawater in the field of dermatological cosmetics and its palliative effects on certain symptoms of skin conditions, such as psoriasis, dermatitis, acne, and eczemas in general, are well-known in the current state of the art. These properties are due to its mineral composition rich in micronutrients such as magnesium, bromine, selenium, strontium, potassium, and calcium, among others, which, due to their ability to mitigate the increase in water loss through the skin, reinforce the barrier affect, hydrate, and accelerate the natural skin repair process.

The different cosmetic treatment products for the skin can be presented to the end consumer in many cosmetic forms, such as lotions, powder, etc. Emulsions are a particularly advantageous cosmetic form because they are easy to apply as a result of their lightweight texture and rapid absorption, and because they provide an immediate sensation of comfort on the skin after application.

More specifically, an emulsion is a more or less homogenous mixture of two immiscible liquids. One of these liquids constitutes the dispersed phase and the other one constitutes the dispersing or continuous phase. To produce the emulsion, the dispersed phase is dispersed in the dispersing phase, where it is sometimes necessary to add an emulsifying agent or surfactant to provide stability to the emulsion.

The main problem to be solved when preparing emulsions is, precisely, the stability thereof, which is understood as the capacity of the emulsion to maintain the homogenous mixture of the aqueous phase and oil phase, without physical separation thereof.

Additionally, this problem is exacerbated in the event of the emulsions containing a seawater- or brine-based aqueous phase, since high concentrations of salt typical of these aqueous phases cause phase separation.

Documents such as patent number ES2593682T3 or patent number JP11228377 disclose oil-in-water cosmetic emulsions which are stable, but they do not solve the drawback of stability of the emulsion associated with a phase having a high concentration of salts, such as seawater.

The invention proposed in the present specification solves the drawback described above by offering an emulsion composition which combines cosmetic and therapeutic compositions with respect to the relief of symptoms of a disease due to the seawater for the skin that is highly stable both physically and microbiologically, as well as the method of producing same.

DESCRIPTION OF THE INVENTION

The emulsion object of the invention comprises the mixture of two phases, specifically an aqueous phase and an oil phase, wherein the aqueous phase comprises seawater.

The emulsion will thereby be produced by mixing, on one hand, all the water-soluble components to produce the aqueous phase, and on the other hand, all the oil-miscible components, in the presence of an emulsifying agent.

In that sense, in addition to the seawater, at least one viscosifier and at least one humectant are present in the aqueous phase of the present invention, whereas the oil phase comprises polyglyceryl, hectorite, propylenecarbonate, t-butyl alcohol, polyacrylate crosspolymer-6, at least one viscosifier, at least one emulsifier, at least one co-emulsifier, and at least one emollient. The elements forming the different phases thereby enable the formation of an emulsion of stabilized, homogenous phases that are not separated from one another.

Therefore, the amount of seawater present in the aqueous phase is in a range between 1% and 90% (w/w) in relation to the total amount of the emulsion. Naturally the higher the percentage of seawater, the higher the electrolyte content, and therefore, the more difficult it will be for the mixture of the phases to reach homogenization and to maintain stability.

On the other hand, the maximum percentages of polyglyceryl, hectorite, propylenecarbonate, t-butyl alcohol, and polyacrylate crosspolymer-6 contained in the oil phase are 20% (w/w) each in relation to the total amount of the emulsion.

The preferred components for the viscosifier, humectant, emollient, and co-emulsifier for the purpose of producing the emulsion of the invention are described in detail below:

Among the viscosifiers that can be used in the aqueous phase and in the oil phase, at least one component selected from the group of an acrylamide copolymer, an acrylate copolymer, an acrylic acid copolymer, xanthan gum, a methacrylate polyglyceryl, a carbomer, and hydroxyethylcellulose can be used.

Among the humectants of the aqueous phase, at least one component selected from the group of glycerin, propyleneglycol, sorbitol, pentaerythritol, polyglycerols, and polyethyleneglycols can be used.

Among the emollients of the oil phase, at least one component selected from the group of isopropyl palmitate, isopropyl myristate, oleyl oleate, isostearyl isostearate, decyl oleate, glyceryl stearate, and diglyceride caprylate can be used.

Among the co-emulsifiers of the oil phase, at least one component selected from the group of cetyl alcohol, lauryl alcohol, stearyl alcohol, oleyl alcohol, cetearyl glucoside, and ceteareth-12 can be used.

The difficulty of the present invention lies in producing a mixture of the stable phases for the purpose of providing a product the composition and presentation of which remain unchanged over time, in a homogenous manner, without phase separation, with all the properties thereof remaining unchanged. To that end, the emulsion will have to be produced by means of the following method of manufacture:

a) Preparing an Aqueous Phase

This step seeks to increase the viscosity of the seawater by means of mixing it with a viscosifier and a humectant. Aqueous phase droplet mobility is thereby decreased, making it more difficult for droplets to collide with one another.

The formation of the aqueous phase is produced by means of the following steps:

introducing seawater, a viscosifier, and a humectant in a reactor, stirring the seawater, viscosifier, and humectant at a speed of at least 10 rpm for at least 20 minutes and at a temperature between 50° C. and 90° C., homogenizing the seawater, viscosifier, and humectant at a speed of at least 1500 rpm for at least 20 minutes and at a temperature between 50° C. and 90° C.

b) Preparing an Oil Phase

In this step, an emulsifying system with the capacity to be stable with respect to a significant amount of electrolytes (present in the seawater) is selected. To that end, surface-active agents which are referred to as emulsifiers and allow reducing the surface tension of the phase that is produced when used to stabilize an emulsion are used. Preferably, this step is carried out in a melting vessel as it is a vessel with heat input, where the elements involved in the oil phase are heated and melted.

The formation of the oil phase is produced by means of the following steps:

introducing polyglyceryl, hectorite, propylenecarbonate, t-butyl alcohol, polyacrylate crosspolymer-6, at least one viscosifier, at least one emulsifier, at least one co-emulsifier, and at least one emollient in a melting vessel, stirring the polyglyceryl, hectorite, propylenecarbonate, t-butyl alcohol, polyacrylate crosspolymer-6, at least one viscosifier, at least one emulsifier, at least one co-emulsifier, and at least one emollient at a speed of at least 10 rpm for at least 20 minutes and at a temperature between 50° C. and 90° C., c) Next, Providing the Conditions Suitable for Formation of the Emulsion The mechanical emulsifying work thereby allows splitting up the phase masses as their surface tension is mechanically overcome.

To that end, the temperature will be an essential parameter as it has a direct influence on surface tension. Therefore, in the case at hand, when the temperature increases, surface tension, tension between phases, and viscosity decrease, favoring the emulsion between phases.

The oil phase is added onto the aqueous phase and stirred at a speed of at least 10 rpm for at least 10 minutes and at a temperature between 50° C. and 90° C. Next, homogenization is performed at a speed of at least 1500 rpm for at least 10 minutes and at a temperature between 50° C. and 90° C., producing a homogenous emulsion with physical stability.

d) Microbiological Stabilization of the Emulsion

To that end, components such as caprylyl glycol and caprylhydroxamic acid are added to the emulsion produced in phase c) to provide it with microbiological stability, where it is advisable for the emulsion to be at a temperature between 20° C. and 40° C.

The combination of the aforementioned elements and the mixing thereof following the described method thereby allows producing an emulsion the oil and aqueous phases of which are homogenous and stable with respect to one another.

The main advantage of the emulsion of the invention is the presence of seawater among the elements of its composition, thereby making it possible to readily apply on the skin a mixture which has a lightweight texture and rapid absorption providing confirmed improvements in the scope of dermatological cosmetics and in certain symptoms of skin conditions such as psoriasis, dermatitis, acne, and eczemas in general. These properties are a result of its mineral composition rich in micronutrients such as magnesium, bromine, selenium, strontium, potassium, and calcium, among others, which, due to their ability to mitigate the increase in water loss through the skin, reinforce the barrier affect, hydrate, and accelerate the natural skin repair process.

PREFERRED EMBODIMENT

The preferred method of manufacture which allows producing the emulsion of the invention is described in detail below:

Seawater and an acrylamide and propyleneglycol copolymer are mixed in a reactor, stirring for 25 minutes at a blade speed of 12 rpm and at a temperature of 70° C.

Next, the working speed is increased to 2000 rpm for 25 minutes for homogenizing the aqueous phase that is produced.

Polyglyceryl, hectorite, propylenecarbonate, t-butyl alcohol, polyacrylate crosspolymer-6, an acrylamide copolymer as a viscosifier, isopropyl myristate as an emollient, and cetyl alcohol as a co-emulsifier are mixed in a melting vessel, and they are stirred at a speed of 15 rpm for 25 minutes and at a working temperature of 70° C. to produce the oil phase.

Next, the oil phase is added in a reactor onto the aqueous phase, maintaining stirring at 15 rpm for 20 minutes and at a temperature of 70° C.; next, homogenization is performed at a speed of 2000 rpm for 20 minutes and at a temperature of 70° C., producing a homogenous emulsion with physical stability.

Finally, to produce the microbiologically stabilized emulsion, caprylyl glycol and caprylhydroxamic acid are added to the emulsion produced in the preceding step at a temperature of 25° C.

The invention claimed is:

1. An emulsion, wherein it contains a mixture of an aqueous phase and an oil phase, wherein the aqueous phase comprises seawater, at least one viscosifier, and at least one humectant, and wherein the oil phase comprises polyglyceryl, hectorite, propylenecarbonate, t-butyl alcohol, polyacrylate crosspolymer-6, at least one viscosifier, at least one emulsifier, at least one co-emulsifier, and at least one emollient, and wherein the emulsion is stabilized, homogenous and without phase separation.

2. The emulsion according to claim 1, wherein the amount of seawater present in the aqueous phase is in a range between 1% and 90% (w/w) in relation to the total amount of the emulsion.

3. The emulsion according to claim 1, wherein the amount of seawater of the aqueous phase is in the form of brine with a boron content less than 1 mg/l, is free of organic components, bacteria and macromolecules having a size greater than $0.1\mu$, and has a pH greater than 8.2.

4. The emulsion according to claim 1, wherein the polyglyceryl, hectorite, propylenecarbonate, t-butyl alcohol, and polyacrylate crosspolymer-6 each has an amount not exceeding 20% (w/w) in relation to the total amount of the emulsion.

5. The emulsion according to claim 1, wherein the viscosifier of the aqueous phase and of the oil phase is at least one component selected from the group consisting of an acrylamide copolymer, an acrylate copolymer, an acrylic acid copolymer, xanthan gum, a methacrylate polyglyceryl, a carbomer, and hydroxyethylcellulose.

6. The emulsion according to claim 1, that wherein the humectant of the aqueous phase is at least one component selected from the group consisting of propyleneglycol, sorbitol, glycerin, pentaerythritol, polyglycerols, and polyethyleneglycols.

7. The emulsion according to claim 1, wherein the emollient of the oil phase is at least one component selected from the group consisting of isopropyl palmitate, isopropyl myristate, oleyl oleate, isostearyl isostearate, decyl oleate, glyceryl stearate, and diglyceride caprylate.

8. The emulsion according to claim 1, wherein the co-emulsifier of the oil phase is at least one component selected from the group consisting of cetyl alcohol, lauryl alcohol, stearyl alcohol, oleyl alcohol, cetearyl glucoside, and ceteareth-12.

9. A method for manufacturing an emulsion, comprising the following steps:
 a) preparing an aqueous phase comprising the steps of:
  introducing seawater, a viscosifier, and a humectant in a reactor,
  stirring the seawater, viscosifier, and humectant at a speed of at least 10 rpm for at least 20 minutes and at a temperature between 50° C. and 90° C.,
  homogenizing the seawater, viscosifier, and humectant at a speed of at least 1500 rpm for at least 20 minutes and at a temperature between 50° C. and 90° C.,
 b) preparing an oil phase comprising the steps of:
  introducing polyglyceryl, hectorite, propylenecarbonate, t-butyl alcohol, polyacrylate crosspolymer-6, at least one viscosifier, at least one emulsifier, at least one co-emulsifier, and at least one emollient in a melting vessel,
  stirring the polyglyceryl, hectorite, propylenecarbonate, t-butyl alcohol, polyacrylate crosspolymer-6, at least one viscosifier, at least one emulsifier, at least one co-emulsifier, and at least one emollient at a speed of at least 10 rpm for at least 20 minutes and at a temperature between 50° C. and 90° C.,
 c) adding the oil phase onto the aqueous phase and stirring at a speed of at least 10 rpm for at least 10 minutes and at a temperature between 50° C. and 90° C., next homogenization is performed at a speed of at least 1500 rpm for at least 10 minutes and at a temperature between 50° C. and 90° C., producing a homogenous emulsion with physical stability, and
 d) adding to the emulsion produced in step c) stabilizing components selected from the group consisting of caprylyl glycol and caprylhydroxamic acid, at a temperature between 20° C. and 40° C., to provide the emulsion with microbiological stability.

\* \* \* \* \*